United States Patent
Misumi

(10) Patent No.: US 9,326,522 B2
(45) Date of Patent: May 3, 2016

(54) MICROBIAL PESTICIDAL COMPOSITION

(75) Inventor: Yuji Misumi, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 133 days.

(21) Appl. No.: 13/884,456

(22) PCT Filed: Nov. 8, 2011

(86) PCT No.: PCT/JP2011/075729
§ 371 (c)(1),
(2), (4) Date: May 10, 2013

(87) PCT Pub. No.: WO2012/063824
PCT Pub. Date: May 18, 2012

(65) Prior Publication Data
US 2013/0236522 A1    Sep. 12, 2013

(30) Foreign Application Priority Data

Nov. 10, 2010  (JP) ................................ 2010-252382

(51) Int. Cl.
| | |
|---|---|
| *A01N 63/00* | (2006.01) |
| *A01N 63/02* | (2006.01) |
| *A01N 59/20* | (2006.01) |
| *C12N 1/20* | (2006.01) |
| *C12N 1/04* | (2006.01) |
| *A01N 59/16* | (2006.01) |

(52) U.S. Cl.
CPC ............... *A01N 63/00* (2013.01); *A01N 63/02* (2013.01); *C12N 1/04* (2013.01); *C12N 1/20* (2013.01)

(58) Field of Classification Search
None
See application file for complete search history.

(56) References Cited

U.S. PATENT DOCUMENTS 6,113,950 A * 9/2000 Foster ........................... 424/617
6,589,524 B1 * 7/2003 Douillet ................... 424/93.462
2008/0194406 A1 * 8/2008 Price et al. .................. 504/116.1
2011/0111957 A1 * 5/2011 Ishaque et al. ................ 504/103
2012/0100094 A1 * 4/2012 Reuter et al. .................. 424/76.6

FOREIGN PATENT DOCUMENTS

| JP | 5 051305 | 3/1993 |
|---|---|---|
| JP | 8 175920 | 7/1996 |
| JP | 8 175921 | 7/1996 |
| JP | 2001 346407 | 12/2001 |
| JP | 2005 206496 | 8/2005 |
| JP | 2006 96753 | 4/2006 |
| JP | 2008 127366 | 6/2008 |
| WO | WO 2009126473 A1 * | 10/2009 |

OTHER PUBLICATIONS

Myasnik M., et al., "Comparative Sensitivity of UV-B Radiation of Two *Bacillus thuringiensis* Subspecies and Other *Bacillus* sp.," Current Microbiology vol. 43 (2001), pp. 140-143.*
Machine translation of JP 2008-127366 (translated to English), translation produced Dec. 11, 2014, p. 1-48.*
"Opinion of the Scientific Panel on Additives and Products or Substances used in Animal Feed on the safety and efficacy of the mirobiological product '035', a preparation of Bacillus subtilis, as a feed additives for chickens for fattening in accordance with Regulation (#C) No. 1831/2003," The EFSA Journal (2006) 406, p. 1-11.*
International Search Report issued Feb. 14, 2012 in PCT/JP11/69470 filed Nov. 8, 2011.

* cited by examiner

*Primary Examiner* — Tracy Vivlemore
*Assistant Examiner* — Monica Shin
(74) *Attorney, Agent, or Firm* — Oblon, McClelland, Maier & Neustadt, L.L.P.

(57) ABSTRACT

[Problem]
A microbial pesticidal composition containing viable spores of a bacterium belonging to the genus *Bacillus* and a chemical pesticide, in which the spores can be preserved stably in a living state for a long period of time, and a method for preserving the spores stably in a living state for a long period of time, are provided.
[Dissolution Means]
Viable spores of *Bacillus subtilis* and/or *Bacillus amyloliquefaciens* are blended with at least one member selected from a metal oxide, a metal hydroxide, a metal oxide silicic acid salt, and a metal hydroxide silicic acid salt.

10 Claims, No Drawings

MICROBIAL PESTICIDAL COMPOSITION

This application is a National Stage of PCT/JP11/075729 filed Nov. 8, 2011 and claims the benefit of JP 2010-252382 filed Nov. 10, 2010.

TECHNICAL FIELD

The present invention relates to a microbial pesticidal composition containing viable spores of a bacterium belonging to the genus *Bacillus*, in which the spores can be preserved stably in a living state for a long period of time, and to a method for preserving the spores stably in a living state for a long period of time.

BACKGROUND ART

Control of plant diseases and pests is an inevitable work in efficiently performing the agricultural production, and in order to achieve this purpose, synthetic pesticides have been used, resulting in making a remarkable achievement. However, in recent years, there have been taken up the appearance of chemical-resistant insect pests and the issue of environmental disruption to be caused due to administration of large dose of synthetic pesticides, and how to reduce the environmental load, thereby performing the agricultural production efficiently and continuously has become an important problem in the agricultural field.

As one of solution strategies thereof, microbial pesticides utilizing functions of microorganisms are proposed. By a single use or combined use thereof with a synthetic pesticide, an effect for reducing the environmental load and an effect for suppressing the frequency of appearance of resistant diseases and pests, which is a serious problem in the synthetic pesticides, are perceived.

At present, as microorganisms which are expected to be utilized as microbial pesticides, non-pathogenic *Fusarium* capable of activating the resistance which a plant originally possesses to control the disease injury; *Trichoderma* exhibiting antibiotic activity against pathogenic microbes; filamentous fungi that are a pathogenic fungus against insect pests; bacteria which infect weeds; and the like are proposed.

In this way, a variety of microorganisms having possibility as pesticides have been proposed. However, in developing microbial pesticides, namely microbial agent for controlling a plant disease and/or a pest, how to make a microorganism that is an active component into a formulation stably in a viable cell state is a key, and the extinction of microorganisms during the preservation period, or the like is an obstacle. In consequence, the development of a method for preserving a microorganism stably in a living state for a long period of time is an important problem.

Now, as for general preservation methods of microorganisms, there are known a freeze-drying method, a method of storing cultures under paraffin oil, a slant medium method, and the like. But, though all of these methods are effective in the case of handling a small-scale amount of microorganisms, they are not suitable as a preservation method of microbial pesticides in which handling of a large amount of microorganisms and a large number of viable cells are required.

On the other hand, as for microbial pesticides or formulations of microbial materials, there have hitherto been known a formulation obtained by adsorbing a microorganism belonging to the genus non-pathogenic *Fusarium* onto a zeolite-based substrate and spontaneously drying it (Patent Document 1); an agent for controlling a plant disease utilizing a sporal fraction of a bacterium belonging to the genus *Bacillus* (Patent Document 2); a composition obtained by mixing an adsorbent having ammonia-adsorbing ability with microorganisms having a controlling effect against the plant disease injury (Patent Documents 3 and 4); a composition composed of endospores of *Bacillus subtilis* and a chemical fungicide component (Patent Document 5); and the like.

However, in the above-described formulation in which viable cells of *Fusarium* are adsorbed onto a zeolite-based substrate, there is a tendency that when preserved at room temperature, the number of viable cells rapidly decreases; and in the case of agent for controlling a plant disease utilizing a sporal fraction of cells belonging to the genus *Bacillus*, how its preservability changes is not known at all. Moreover, in the case of microorganism materials, since the substrate used as a culture medium is incorporated as it is, there is involved such a problem that nutrient components exist and promote the growth of pathogenic microbes during the preservation. On the other hand, the above-described composition having an adsorbent having ammonia-adsorbing ability mixed therewith involved such problems that in pesticide formulations including the addition of water during the formulation step, they cannot be applied because of deactivation of the adsorbing ability of the adsorbent to be caused due to the addition of water; and that sufficient preservation stability is not always obtained in the long-term preservation over several years. In addition, the mixed composition of endospores of *Bacillus subtilis* and a chemical fungicide involved such a problem that the viable spores decrease due to the chemical fungicide component to have been mixed.

PRIOR ART DOCUMENT

Patent Document

Patent Document 1: JP-A-63-227507
Patent Document 2: JP-A-8-175919
Patent Document 3: JP-A-2000-264808
Patent Document 4: JP-A-2000-264807
Patent Document 5: JP-T-6-511258

SUMMARY OF THE INVENTION

Problem to be Solved by the Invention

An object of the present invention is to provide a microbial pesticidal composition (mixed pesticidal composition) containing viable spores of a bacterium belonging to the genus *Bacillus* and a chemical pesticide, in which the spores can be preserved stably in a living state for a long period of time, and a method for preserving the spores stably in a living state for a long period of time.

Means for Solving the Problem

The present inventor made various extensive and intensive investigations regarding microbial pesticidal compositions. As a result, it has been found that in a microbial pesticidal composition comprising a blend of viable spores of *Bacillus subtilis* and/or *Bacillus amyloliquefaciens* and at least one member selected from a metal oxide, a metal hydroxide, a metal oxide silicic acid salt, and a metal hydroxide silicic acid salt, the preservability of the spores is favorable, leading to accomplishment of the present invention on the basis of such knowledge.

Specifically, embodiments of the present invention are as follows.

(1) A microbial pesticidal composition comprising a blend of viable spores of *Bacillus subtilis* and/or *Bacillus amyloliquefaciens* and at least one member selected from a metal oxide, a metal hydroxide, a metal oxide silicic acid salt, and a metal hydroxide silicic acid salt.
(2) The microbial pesticidal composition described in (1) above, wherein a micro granule or granule containing viable spores of *Bacillus subtilis* and/or *Bacillus amyloliquefaciens* is used as an inner core, and the surface of the inner core is covered by at least one member selected from a metal oxide, a metal hydroxide, a metal oxide silicic acid salt, and a metal hydroxide silicic acid salt.
(3) The microbial pesticidal composition described in (2) above, wherein a mean particle diameter of the micro granule (in Japanese, bihuntai) containing viable spores of *Bacillus subtilis* and/or *Bacillus amyloliquefaciens* is from 0.05 to 5 mm, and a volume median diameter (in Japanese, taiseki chuuikei) of the at least one member selected from a metal oxide, a metal hydroxide, a metal oxide silicic acid salt, and a metal hydroxide silicic acid salt is from 0.01 to 250 µm.
(4) The microbial pesticidal composition described in (3) above, wherein a ratio of the mean particle diameter of the micro granule containing viable spores of *Bacillus subtilis* and/or *Bacillus amyloliquefaciens* to the volume median diameter of the at least one member for covering the surface of the inner core, which is selected from a metal oxide, a metal hydroxide, a metal oxide silicic acid salt, and a metal hydroxide silicic acid salt ((mean particle diameter of the micro granule)/(volume median diameter of the metal oxide or metal hydroxide)), is from 5 to 750.
(5) The microbial pesticidal composition described in any one of (1) to (4) above, wherein the metal oxide is at least one member selected from oxides of zinc, aluminum, iron, titanium, and magnesium; the metal hydroxide is at least one member selected from hydroxides of aluminum, iron, magnesium, and copper; and the metal oxide silicic acid salt or metal hydroxide silicic acid salt is aluminum oxide silicic acid salt.
(6) The microbial pesticidal composition described in any one of (1) to (5) above, further comprising a surfactant.
(7) The microbial pesticidal composition described in (6) above, wherein the surfactant is blended in the inner core, and moreover the surface of the inner core is also covered by the surfactant together with the at least one member selected from a metal oxide, a metal hydroxide, a metal oxide silicic acid salt, and a metal hydroxide silicic acid salt.
(8) The microbial pesticidal composition described in (6) above, wherein the surfactant is combined only in the inner core.
(9) The microbial pesticidal composition described in (6) above, wherein the surfactant is covered on only the surface of the inner core together with the at least one member selected from a metal oxide, a metal hydroxide, a metal oxide silicic acid salt, and a metal hydroxide silicic acid salt (the surfactant is not contained in the inner core).
(10) The microbial pesticidal composition described in any one of (6) to (9) above, wherein the surfactant is an anionic surfactant.
(11) The microbial pesticidal composition described in (10) above, wherein the surfactant is at least one member selected from a lignin sulfonic acid salt, an alkyl benzene sulfonic acid salt, a naphthalene sulfonic acid salt, and a dialkyl sulfosuccinate salt.
(12) The microbial pesticidal composition described in any one of (1) to (11) above, wherein a water content in the total mass of the composition is less than 2.5% by mass (preferably less than 1.5% by mass).
(13) A method for preserving viable spores in a microbial pesticidal composition stably in a living state for a long period of time, which comprises using, as an inner core, a micro granule or granule containing viable spores of *Bacillus subtilis* and/or *Bacillus amyloliquefaciens* and covering the surface of the inner core by at least one member selected from a metal oxide, a metal hydroxide, a metal oxide silicic acid salt, and a metal hydroxide silicic acid salt.

Effect of the Invention

According to the present invention, viable spores in a microbial pesticidal composition, containing viable spores of a bacterium belonging to *Bacillus subtilis* or *Bacillus amyloliquefaciens* and at least one member selected from a metal oxide, a metal hydroxide, a metal oxide silicic acid salt, and a metal hydroxide silicic acid salt, can be preserved stably in a living state for a long period of time.

MODES FOR CARRYING OUT THE INVENTION

The microbial pesticidal composition according to the present invention contains, as an active component, spores (endospores) of *Bacillus subtilis* or *Bacillus amyloliquefaciens*. In addition, a mixture of these spores may also be used.

The bacterium belonging to *Bacillus subtilis* or *Bacillus amyloliquefaciens*, which is used in the present invention, is not particularly limited. However, those which antagonize against plant pathogenic fungi and bacteria are preferably exemplified. Above of all, *Bacillus* sp. D747 is more preferable.

This *Bacillus* sp. D747 strain is a bacterial strain which was isolated from the air in Kikugawa-shi, Shizuoka-ken, Japan and deposited in the International Patent Organism Depositary of the National Institute of Advanced Industrial Science and Technology (Tsukuba Central 6, 1-1, Higashi 1-chome Tsukuba-shi, Ibaraki-ken, 305-8566, Japan) on Nov. 28, 2000. Then, the Strain was transferred to be deposited under the Budapest Treaty on Nov. 8, 2002, as *Bacillus* sp. D747 with new Accession Number of FERM BP-8234.

The bacterial characteristics of the *Bacillus* sp. D747 strain are described as follows. Incidentally, the tests for the bacterial characteristics were carried out in accordance with Bergey's Manual of Systematic Bacteriology, Volume 1 (1984).
(A) Morphological characteristics:
Morphology: *bacillus*
Size: 1.0 to 1.2 µm width, 3 to 5 µm length
Mobility: +
Flageller adherent condition: Periphery flagella
Endospore: +
Spore Position: center
Spore swelling: −
(B) Cultural Characteristics:
Color of colony: white to pale brown
Culturing in bouillon agar plate medium: A white to cream-colored colony is formed, and the surface is wrinkled.
(C) Physiological Characteristics:
Gram's stain stainability: +
Nitrate reduction: +
MR test: −
VP test: +
Indole formation: −
Starch hydrolysis: +
Citric acid assimilating ability: +
Inorganic nitrogen source: +
Oxidase: −

Catalase: +
Growth pH:
　6.8, Bouillon medium: +
　5.7, Bouillon medium: +
Growth temperature:
　30° C.: +
　50° C.: −
Growth NaCl concentration:
　2%: +
　5%: +
　7%: +
Aerobic growth: +
Anaerobic growth: —
O—F test: 0
Yolk reaction: −
Acid formation from glucose: +
Acid formation from mannitol: −
Acid formation from L-arabinose: −
Acid formation from D-xylose: −
Gas formation from glucose: −
β-Galactosidase: −
NaCl and KCl requiring property: −

In the microbial pesticidal composition according to the present invention, though *Bacillus* sp. D747 which is able to control the above-described undesirable plant disease injury can be used solely, a valiant of the D747 strain can also be employed alone or in combination with the D747 strain. The variant has the above-described bacterial characteristics of the D747 strain and exhibit effects of controlling plant disease injury, and it is also possible to utilize a spontaneous mutant strain, a mutant strain produced by using ultraviolet rays or a chemical mutagen agent, a cell fusion strain, or a genetic recombination strain.

The viable spore which is used in the present invention is obtained from cultures of bacteria belonging to the above-described *Bacillus subtilis* or *Bacillus amyloliquefaciens*. The culture of a bacterium belonging to the genus *Bacillus* can be performed according to usual culture methods of a bacterium belonging to the genus *Bacillus*, for example, reciprocating shaking culture, jar-fermentor culture, liquid culture using a culture tank, etc., solid culture, or the like. For example, in addition to a common medium such as a meat extract medium, etc., there are exemplified media containing glucose, peptone, yeast extract, or the like, and so on. In addition, besides a liquid medium, solid media such as a slant medium, a plate medium etc. may also be used. By culturing, the bacterium belonging to the genus *Bacillus* multiplies, so that by means of culture, a desired amount of the cells can be obtained.

As a carbon source of the medium, all of sources which the above-described bacteria belonging to *Bacillus subtilis* or *Bacillus amyloliquefaciens* are able to assimilate can be utilized. For example, in addition to sugars such as glucose, galactose, lactose, sucrose, maltose, malt extract, starch hydrolysates, etc., there can be exemplified various synthetic or natural carbon sources which bacteria belonging to the genus *Bacillus* can utilize. Similarly, as a nitrogen source of the medium, it is possible to utilize not only organic nitrogen-containing materials such as peptone, meat extract, yeast extract, etc., but various synthetic or natural materials which the foregoing bacteria can be utilized. Inorganic salts such as sodium chloride, a phosphoric acid salt, etc., salts of a metal such as calcium, magnesium, iron, etc., or micro nutrient sources such as vitamins, amino acids, etc. can also be added according to the customary method of microbial culture, if necessary. These may be properly designed grasping detailed mycological characteristics of a bacterial strain which is actually used, and the like.

The culture can be carried out under aerobic conditions such as shaking culture, aeration culture, etc. It is suitable that the culture temperature ranges from 20 to 30° C., and preferably ranges from 25 to 30° C.; that the pH ranges from 5 to 8, and preferably ranges from 6 to 7; and that the culture period suitably ranges from 1 to 4 days, and preferably ranges from 2 to 3 days.

As for a method for separating the viable spores from the culture of the bacterium belonging to *Bacillus subtilis* or *Bacillus amyloliquefaciens* obtained as described above, the separation can be performed adopting a method such as membrane separation, centrifugation, filtration separation, etc. Though the obtained sporal fraction may be used for the microbial pesticidal composition according to the present invention as it is (in a state where water is contained in some extent), it is preferable to use the sporal fraction upon being formed into a dry material adopting a known drying method such as ventilation drying (through-flow drying), spray drying, fluidized bed drying, etc.

In the case of obtaining a particulate dry material (dry granule) from such a sporal fraction of the bacterium belonging to *Bacillus subtilis* or *Bacillus amyloliquefaciens*, it is preferable that the raw materials of a pesticide formulation are respectively mixed in prescribed proportions, and after being pulverized according to the need, a prescribed proportion of the sporal fraction is added, followed by performing a general granulation method such as an extrusion granulation method, a fluidized bed granulation method, a spray dry granulation method, a tumbling granulation method, dry compaction, etc. However, other method may also be adopted. In the case where the resulting particulate dry material is used as an inner core, and the surface of the inner core is covered by at least one member selected from a metal oxide, a metal hydroxide, a metal oxide silicic acid salt, and a metal hydroxide silicic acid salt, a particulate matter in which irregularities are present on the surface of the particulate dry material is preferable, and an amorphous coagulated particulate matter obtained by means of fluidized bed granulation is especially preferable.

In the present invention, though the metal oxide, the metal hydroxide, the metal oxide silicic acid salt, or the metal hydroxide silicic acid salt is not particularly limited, examples thereof include oxides or hydroxides of sodium, magnesium, aluminum, potassium, calcium, scandium, titanium, vanadium, chromium, manganese, iron, cobalt, nickel, copper, zinc, gallium, germanium, rubidium, strontium, molybdenum, rhodium, silver, tin, barium, tungsten, and iridium, and silicic acid salts of these oxides or hydroxides. Of these, oxides of zinc, aluminum, iron, titanium, and magnesium, hydroxides of aluminum, iron, magnesium, and copper, and silicic acid salts of aluminum oxide are suitably used. Active alumina, natural zeolite, and synthetic zeolite are most suitably used. As for these oxides or hydroxides, commercially available products as reagents or industrial chemicals can also be used.

In the present invention, though the metal oxide, the metal hydroxide, the metal oxide silicic acid salt, or the metal hydroxide silicic acid salt is not particularly limited, in the case of being processed into an agricultural and horticultural composition, when it is used as a dust in other words as a powder, the processing is easily performed. In particular, a material having a volume median diameter (particle diameter at the time when the number of particles in the particle size distribution determined by sieving using a prescribed sieve and measuring the weight for every particle size accounts for 50% of the whole: in Japanese, taiseki chuuikei)) of from 0.01 to 250 lam is easily processed, and a material having a volume median diameter of from 0.1 to 50 is more easily processed.

The microbial pesticidal composition according to the present invention is a microbial pesticidal composition comprising a blend of viable spores of *Bacillus subtilis* or *Bacillus amyloliquefaciens* and at least one member selected from a metal oxide, a metal hydroxide, a metal oxide silicic acid salt, and a metal hydroxide silicic acid salt, and it can be obtained as a mixture of the dried viable spores and the metal exide etc. and, if necessary, auxiliary raw materials for a pesticide formulation, in which said dried viable spores are able to take the form of dust (fine powder, micro granule), or granule, or mixture thereof (dust-granule mixture), and said metal oxide etc. is able to be a dust or granule of at least one member selected from a metal oxide, a metal hydroxide, a metal oxide silicic acid salt, and a metal hydroide silicic acid salt.

Though a mixing method thereof is not particularly limited, the mixing can be performed using a Nauta mixer, a ribbon mixer, or the like, which is frequently used in the usual production of a pesticide formulation, and a pulverizer such as an impact pulverizer, etc. can also be applied.

It is preferable that the viable spores of *Bacillus subtilis* or *Bacillus amyloliquefaciens*, which comprise the microbial pesticidal composition according to the present invention, are used as a micro granule or granular matter obtained by drying the sporal fraction; and that the at least one member selected from a metal oxide, a metal hydroxide, a metal oxide silicic acid salt, and a metal hydroxide silicic acid salt is used as the dust or powder. Furthermore, it is preferable that the micro granule or granule containing viable spores of *Bacillus subtilis* or *Bacillus amyloliquefaciens* is used as an inner core, and the surface of the inner core is covered by at least one member selected from a metal oxide, a metal hydroxide, a metal oxide silicic acid salt, and a metal hydroxide silicic acid salt. For covering the surface of the inner core, in addition to the at least one member selected from a metal oxide, a metal hydroxide, a metal oxide silicic acid salt, and a metal hydroxide silicic acid salt, a pesticidal component and an adjuvant of a pesticide formulation, such as a surfactant, a carrier, etc., can be mixed and used, if necessary.

In the microbial pesticidal composition according to the present invention, in which a micro granule or granule containing viable spores of *Bacillus subtilis* or *Bacillus amyloliquefaciens* is used as an inner core, and the surface of the inner core is covered by at least one member selected from a metal oxide, a metal hydroxide, a metal oxide silicic acid salt, and a metal hydroxide silicic acid salt, a mean particle diameter of the micro granule or granule containing viable spores of *Bacillus subtilis* or *Bacillus amyloliquefaciens* preferably ranges from 0.05 to 5 mm, and more preferably ranges from 0.1 to 2.5 mm. The mean particle diameter of the granule can be easily determined as a mean mass diameter (in Japanese, ruiseki chuuikei: particle diameter at an accumulated value of 50% in the particle size distribution) by sieving using a prescribed screen and measuring the weight of the micro granule or granule for every particle size.

In addition, the volume median diameter of the at least one member selected from a metal oxide, a metal hydroxide, a metal oxide silicic acid salt, and a metal hydroxide silicic acid salt, which covers the surface of the inner core, is preferably from 0.01 to 250 μm, and more preferably from 0.1 to 50 μm. In the case when, in addition to at least one member selected from a metal oxide, a metal hydroxide, a metal oxide silicic acid salt, and a metal hydroxide silicic acid salt, an auxiliary raw materials for a pesticide formulation, such as a pesticidal component, a surfactant, a carrier, etc. is mixed, if necessary, followed by performing covering, the volume median diameter of the whole of a powder premix to be covered is also preferably from 0.01 to 250 μm, and more preferably from 0.1 to 50 μm.

Furthermore, a ratio of the mean particle diameter of the micro granule containing viable spores of *Bacillus subtilis* or *Bacillus amyloliquefaciens* to the volume median diameter of the at least one member for covering the surface of the inner core, which is selected from a metal oxide, a metal hydroxide, a metal oxide silicic acid salt, and a metal hydroxide silicic acid salt ((mean particle diameter of the micro granule)/(volume median diameter of the at least one member selected from a metal oxide, a metal hydroxide, a metal oxide silicic acid salt, and a metal hydroxide silicic acid salt)), is preferably from 5 to 750, more preferably from 10 to 500, and most preferably from 20 to 200.

In the present invention, in the case where a micro granule or particulate matter (granule) containing viable spores of *Bacillus subtilis* or *Bacillus amyloliquefaciens* is used as an inner core, and the surface of the inner core is covered by at least one member selected from a metal oxide, a metal hydroxide, a metal oxide silicic acid salt, and a metal hydroxide silicic acid salt, the covering can be performed by mixing the micro granule or granule containing viable spores of *Bacillus subtilis* or *Bacillus amyloliquefaciens* with the at least one member selected from a metal oxide, a metal hydroxide, a metal oxide silicic acid salt, and a metal hydroxide silicic acid salt. Though the mixing is not particularly limited, the mixing can be performed using a mixer which is frequently used in the usual production of a pesticide formulation, and a Nauta mixer and a ribbon mixer, in which mild mixing conditions can be set up, are suitably used.

The microbial pesticidal composition according to the present invention may include other pesticidal components which conforms to the subject to control, such as fungicides, insecticides, acaricides, nematocides, herbicides, plant growth regulators, phytotoxicity reducing components, etc. These pesticidal components are a component which is commercially available or is known as a pesticidal component. These components are known by Pesticide Handbook (Noyaku Handbook), published by Japan Plant Protection Association; Pesticide Manual (Noyaku Soran), published by Japan Plant Protection Association; Kumiai Noyaku Soran, published by Zen-Noh; SHIBUYA INDEX, published by Zen-Noh; and the like.

Among the pesticidal components, as specific examples of the fungicidal component, for example, those selected from BAG-010 (code No.), BAF-045 (code No.), copper dioctanoate, DBEDC, SYP-Z-048 (code No.), TPTA, TPTC, TPTH, acibenzolar-5-methyl, azoxystrobin, amisulbrom, aldimorph, isotianil, isopyrazam, isoprothiolane, ipconazole, iprodione, iprovalicarb, iprobenfos, imazalil, iminoctadine-albesilate, iminoctadine-triacetate, imibenconazole, echlomezole, ethaboxam, edifenphos, ethoxyquin, etridiazole, enestroburin, epoxiconazole, oxadixyl, oxazinylazole, oxycarboxin, oxytetracycline, oxpoconazole-fumarate, oxolinic acid, octhilinone, ofurace, orysastrobin, o-phenylphenol, kasugamycin, captafol, carpropamid, carbendazim, carboxin, quinoxyfen, chinomethionat, captan, quintozene, guazatine, kresoxim-methyl, chloroneb, chlorothalonil, cyazofamid, diethofencarb, diclocymet, dichlofluanid, diclomezine, dicloran, dithianon, diniconazole, zineb, dinocap, diphenyl, diphenylamine, difenoconazole, difenzoquat, cyflufenamid, diflumetorim, cyproconazole, cyprodinil, simeconazole, dimethomorph, cymoxanil, dimoxystrobin, ziram, silthiofam, streptomycin, spiroxamine, sedaxane, zoxamide, dazomet, thiadiazine, tiadinil, thiabendazole, thiram, thiophanate-methyl, thifluzamide, tecnazene, tecloftalam, tetraconazole, debacarb, tebuconazole, tebufloquin, dodine, dodemorph, triadimenol, triadimefon, triazoxide, tricyclazole, triticonazole, tridemorph, triflumizole, trifloxystrobin, triforine, tolylfluanid, tolclofos-methyl, tolnifanide, nabam, nitrothal-isopropyl, nuarimol, validamycin, valifenalate, bixafen, picoxystrobin, bitertanol, hydroxyisoxazole, piperalin, hymexazol, pyraclostrobin, pyrazophos, pyriofenone, pyrifenox, pyributicarb, pyribencarb, pyrimethanil, pyroquilon, vinclozolin, ferbam, famoxadone, phenazine oxide, fenamidone, fenarimol, fenoxanil, ferimzone, fenbuconazole, fenfuram, fenpropidin, fenpropimorph, fenhexamid, folpet, phthalide, bupirimate, fuberidazole, blasticidin-S, furametpyr, furalaxyl, fluazinam, fluoxastrobin, fluopicolide, fluopyram, fluoroimide, fluquinconazole, fludioxonil, flusilazole, flusulfamide, flutianil, flutolanil, flutriafol, flumorph, proquinazid, prochloraz, procymidone, prothioconazole, bronopol, propamocarb hydrochloride, propiconazole, propineb, probenazole, bromuconazole, hexaconazole, benalaxyl, benalaxyl-M, benomyl, pefurazoate, penconazole, pencycuron, benthiavalicarb-isopropyl, penthiopyrad, penflufen, boscalid, fosetyl-aluminium, polyoxin, polycarbamate, mancopper, mandipropamid, mancozeb, maneb, myclobutanil, mildiomycin, methasulfocarb, metam, metalaxyl, metalaxyl-M, metconazole, metominostrobin, metrafenone, mepanipyrim, mepronil, oxyquinoline sulfate, silver, copper compounds such as Bordeaux mixture, basic copper chloride (copper oxychloride), cuprous oxide, copper hydroxide, copper sulfate, oxine copper, copper nonylphenyl sulfonate, etc., sulfur compounds, potassium bicarbonate, sodium bicarbonate, fatty acid glyceride, Lentinura edodes mycelia extract, and microbial pesticides such as a bacterium belonging to the genus *Erwinia*, a bacterium belonging to the genus *Pseudomonas*, a bacterium belonging to the genus *Xanthomonas*, a bacterium belonging to the genus *Bacillus*, a microbe belonging to the genus Talaromyces, a microbe belonging to the genus *Trichoderma*, a microbe belonging to the genus *Fusarium*, and a microbe belonging to the genus *Gliocladium* can be used.

As specific examples of the insecticidal component, the acaricidal component, and the nematocidal component, for example, those selected from 1,3-dichloropropene, BPMC, BPPS, BRP, CL900167 (code No.), cryolite, CVMP, CYAP, DCIP, D-D, DDVP, DEP, DMTP, DNOC, ECP, EPN, MEP, MIPC, MPP, NAC, ammonium N-methyldithiocarbamate (NCS), NI-30 (code No.), NNI-0101, PAP, PHC, RU15525 (code No.), thiazosulfen, XMC, ZXI-8901 (code No.), acrinathrin, azamethiphos, azinphos-ethyl, azinphos-methyl, acequinocyl, acetamiprid, acetoprol, acephate, azocyclotin, abamectin, amitraz, alanycarb, aldicarb, alpha-cypermethrin, allethrin, isocarbophos, isoxathion, isofenphos-methyl, isoprocarb, imicyafos, imidacloprid, imiprothrin, indoxacarb, esfenvalerate, ethiofencarb, ethion, ethiprole, disulfoton, etoxazole, etofenprox, ethoprophos, emamectin, empenthrin, oxamyl, oxydemeton-methyl, omethoate, sodium oleate, metam-sodium, cadusafos, kadethrin, karanjin, cartap, carbaryl, carbosulfan, carbofuran, gamma-cyhalothrin, xylylcarb, quinalphos, kinoprene, chinomethionat, coumaphos, clothianidin, clofentezine, chromafenozide, chlorethoxyfos, chlorantraniliprole, chlordane, chloropicrin, chlorpyrifos, chlorpyrifos-methyl, chlorfenapyr, chlorfenvinphos, chlorfluazuron, chlormephos, cyazypyr, cyanophos, diafenthiuron, cyantraniliprole, dienochlor, cyenopyrafen, dicrotophos, dichlofenthion, cycloprothrin, dicofol, dicyclanil, dinotefuran, dinobuton, cyhalothrin, cyphenothrin, cyfluthrin, diflubenzuron, cyflumetofen, diflovidazin, cyhexatin, cypermethrin, dimethylvinphos, dimethoate, silafluofen, cyromazine, spinosad, spinetoram, spirodiclofen, spirotetramat, spiromesifen, sulcofuron-sodium, sulfluramid, sulprofos, sulfoxaflor, sulfotep, zeta-cypermethrin, diazinon, tau-fluvalinate, thiacloprid, thiamethoxam, thiodicarb, thiocyclam, thiosultap, thiofanox, thiometon, tetrachlorvinphos, tetradifon, tetrame ran, tebupirimfos, tebufenozide, tebufenpyrad, tef uthrin, teflubenzuron, demeton-5-methyl, temephos, rotenone, deltamethrin, terbufos, tralomethrin, transfluthrin, triazamate, triazophos, trichlorfon, triflumuron, trimethacarb, tolfenpyrad, naled, nicotine, nitenpyram, nemadectin, novaluron, noviflumuron, hydroprene, vamidothion, parathion, parathion-methyl, halfenprox, halofenozide, bioallethrin, bioresmethrin, bistrifluoron, hydramethylnon, bifenazate, bifenthrin, pymetrozine, pyraclofos, pyridaphenthion, pyridaben, pyridalyl, pyrifluquinazon, pyriproxyfen, pirimicarb, pyrimidifen, pirimiphos-methyl, pyrethrins, famphur, fipronil, fenazaquin, fenamiphos, phenisobromolate, fenitrothion, fenoxycarb, fenothiocarb, phenothrin, fenobucarb, fenthion, phenthoate, fenvalerate, fenpyroximate, fenpropathrin, butocarboxim, butoxycarboxim, buprofezin, furathiocarb, prallethrin, fluacrypyrim, flucycloxuron, flucythrinate, fluvalinate, flupyrazofos, flufenerim, flufenoxuron, flubendiamide, flumethrin, prothiofos, flonicamid, propaphos, propargite, profenofos, propetamphos, propoxur, bromopropylate, beta-cypermethrin, beta-cyfluthrin, hexaflumuron, hexythiazox, heptenophos, permethrin, bensultap, benzoepin (endosulfan), benzoximate, bendiocarb, benfuracarb, phoxim, phosalone, fosthiazate, phosphamidon, phosmet, formetanate, phorate, petroleum oils, malathion, milbemectin, mecarbam, mesulfenfos, methomyl, metaldehyde, metaflumizone, methamidophos, metham-potassium, metham-ammonium, methiocarb, methidathion, methyl isothiocyanate, methoxychlor, methoxyfenozide, methothrin, metofluthrin, methoprene, metholcarb, mevinphos, monocrotophos, lambda-cyhalothrin, lufenuron, resmethrin, lepmectin, propylene glycol mono fatty acid esters (propylene glycol monolaurate), nicotine sulfate, levamisol hydrochloride (levamisol), ethylene oxide, fenbutatin oxide, fatty acid glyceride, morantel tartrate, rapeseed oil, starch, soybean lecithin, BT agent, *Verticillium lecanii, Pasteuria penetrans, Steinernema carpocapsae,* and *Paecilomyces fumosoroseus* can be used. The BT agent as referred to herein is a general term of pesticides utilizing *Bacillus thuringiensis* as a bacterium, and it includes a crystal protein produced by the bacterium, a viable bacterial spore, and a mixture of the both. In the present invention, all of them can be used.

As specific examples of the herbicidal component, for example, those selected from 2,3,6-TBA, 2,4-D (including salts with amine, diethylamine, triethanolamine, isopropylamine, sodium, lithium, etc.), 2,4-DB, 2,4-PA, ACN, AE-F-150944 (code No.), CAT, DBN, DCBN, DCMU, DCPA, DNOC (including salts with amine, sodium, etc.), DPA, EPTC, IPC, MCPA, MCPA-isopropylamine salt, MCPA-ethyl, MCPA-sodium, MCPP, MDBA, MDBA-isopropylamine salt, MDBA-sodium salt, PAC, SAP, S-metolachlor, SYP-298 (code No.), SYP-300 (code No.), TCA (including salts with sodium, calcium, ammonium, etc.), TCTP, ioxynil, ioxynil-octanoate, aclonifen, acrolein, azafenidin, acifluorfen-sodium, azimsulfuron, asulam, acetochlor, atrazine, anilofos, amicarbazone, amidosulfuron, amitrole, aminopyralid, amiprophos-methyl, ametryn, alachlor, alloxydim, isouron, isoxachlortole, isoxaflutole, isoxaben, isoproturon, ipfencarbazone, imazaquin, imazapic (including salts with amine, etc.), imazapyr (including salts with isopropylamine, etc.), imazamethabenz-methyl, imazamox (including salts with amine, etc.), imazethapyr (including salts with amine, etc.), imazosulfuron, indaziflam, indanofan, esprocarb, ethametsulfuron-methyl, ethalfluralin, ethidimuron, ethoxysulfuron, ethoxyfen-ethyl, ethofumesate, etobenzanid, endothal-disodium, oxadiazon, oxadiargyl, oxaziclomefone, oxasulfuron, oxyfluorfen, oryzalin, orthosulfamuron, orbencarb, cafenstrole, carfentrazone-ethyl, karbutilate, carbetamide, quizalofop-P-ethyl, quizalofop-P-tefuryl, quizalofopethyl, quinoclamine, quinclorac, quinmerac, cumyluron, glyphosate (including salts with sodium, potassium, amine, propylamine, isopropylamine, dimethylamine, trimesium, etc.), glufosinate (including salts with amine, sodium, etc.), clethodim, clodinafop-propargyl, clopyralid, clomazone, chlomethoxyfen, clomeprop, cloransulam-methyl, chloramben, chloridazon, chlorimuron-ethyl, chlorsulfuron, chlorthal-dimethyl, chlorthiamid, chlorphthalim, chlorflurenol (including lower alkyl esters), chlorpropham, chlorbromuron, chloroxuron, chlorotoluron, saflufenacil, cyanazine, diuron, dicamba (including salts with amine, diethylamine, isopropylamine, diglucolamine, sodium, lithium, etc.), cycloate, cycloxydim, diclosulam, cyclosulfamuron, dichlobenil, diclofop-methyl, dichlorprop-P, diquat(-dibromide), dithiopyr, siduron, dinitramine, cinidon-ethyl, cinosulfuron, dinoterb, cyhalofop-butyl, diphenamid, difenzoquat, diflufenican, diflufenzopyr, simazine, dimethachlor, dimethametryn, dimethenamid, simetryn, dimepiperate, dimefuron, cinmethylin, sulcotrione, sulfentrazone, sulfosulfuron, sulfometuron-methyl, sethoxydim, terbacil, daimuron, dalapon, thiazopyr, thiencarbazone, tiocarbazil, thiobencarb, thidiazimin, thidiazuron, thifensulfuron-methyl, n-decanol, desmedipham, desmetryne, tetrapion, thenylchlor, tebutam, tebuthiuron, tepraloxydim, tefuryltrione, terbuthylazine, terbutryn, terbumeton, tembotrione, topramezone, tralkoxydim, triaziflam, triasulfuron, tri-allate, trietazine, triclopyr(-butotyl), tritosulfuron, triflusulfuron-methyl, trifluralin, trifloxysulfuron-sodium, tribenuron-methyl, naptalam (including salts with sodium, etc.), naproanilide, napropamide, nicosulfuron, neburon, norflurazon, vernolate, paraquat dichloride, haloxyfop-methyl, haloxyfop-P-methyl, halosulfuron-methyl, bilanafos-sodium, picloram, picolinafen, bicyclopyrone, bispyribac-sodium, pinoxaden, bifenox, piperophos, pyraclonil, pyrasulfotole, pyrazoxyfen, pyrazosulfuronethyl, pyrazolynate, pyraflufen-ethyl, pyridafol, pyrithiobacsodium, pyridate, pyriftalid, pyributicarb, pyribenzoxim, pyrimisulfan, pyriminobac-methyl, pyroxasulfone, pyroxsulam, fenuron, fenoxasulfone, fenoxaprop-P-ethyl, fenoxaprop-ethyl, fenclorim, fenthiaprop-ethyl, fentrazamide, phenmedipham, foramsulfuron, butachlor, butafenacil, butamifos, butylate, butroxydim, flazasulfuron, flampropmethyl, flamprop-M-methyl, flamprop-ethyl, flamprop-isopropyl, flamprop-M-isopropyl, primisulfuron-methyl, fluazifop-butyl, fluazifop-P-butyl, fluazolate, fluometuron, fluoroglycofen-ethyl, flucarbazone-sodium, flucetosulfuron, fluthiacet-methyl, flupyrsulfuron-methyl-sodium, flufenacet, flufenpyr-ethyl, flupropanate-sodium, flupoxam, flumioxazin, flumiclorac-pentyl, flumetsulam, fluridone, flurtamone, fluoroxypyr, fluorochloridone, pretilachlor, prodiamine, prosulfuron, prosulfocarb, propaquizafop, propachlor, propazine, propanil, propyzamide, propisochlor, propyrisulfuron, propham, profluazol, propoxycarbazone-sodium, profoxydim, bromacil, prometryn, prometon, bromoxynil (including esters with butyric acid, octanoic acid, heptanoic acid, etc.), bromobutide, florasulam, hexazinone, bethrodine (benefin), pethoxamid, benazolin, penoxsulam, beflubutamid, pebulate, bencarbazone, benzfendizone, bensulide, bensulfuron-methyl, benzobicyclon, benzofenap, bentazone (including salts with sodium, etc.), pentanochlor, benthiocarb, pendimethalin, pentoxazone, benfluralin, benfuresate, fosamine-ammonium, fomesafen, mecoprop-potassium, mecoprop-P-potassium, mesosulfuron-methyl, mesotrione, metazachlor, methabenzthiazuron, metazosulfuron, metamitron, metamifop, methyldymron, metoxuron, metosulam, metsulfuron-methyl, metobromuron, metobenzuron, metolachlor, metribuzin, mepiquat-chloride, mefenacet, monolinuron, molinate, iodosulfuron-methyl-sodium, lactofen, linuron, rimsulfuron, lenacil, *Xanthomonas campestris*, and *Drechslera monoceras* can be used.

As specific examples of the plant growth regulating component, for example, those selected from α-naphthalene acetamide, 1-methylcyclopropene, 2,6-diisopropylnaphthalene, 4-CPA, aviglycine, abscisic acid, ancymidol, inabenfide, indole acetic acid, indole butyric acid, uniconazole-P, ethychlozate, ethephon, oxine-sulfate, carvone, calcium formate, cloxyfonac-sodium, cloxyfonac-potassium, cloprop, chlormequat, choline, cytokinins, cyanamide, cyclanilide, dichlorprop, dikegulac, gibberellin, dimethipin, sintofen, daminodide, n-decyl alcohol, 1-triacontanol, trinexapac-ethyl, paclobutrazol, paraffin, butralin, flumetralin, flurprimidol, flurenol, prohydrojasmon, prohexadione-calcium, (6-) benzylaminopurine, forchlorfenuron, maleic hydrazide, mepiquat-chloride, mefluidide, wax, MCPA-thioethyl, MCPB, 4-CPA, calcium chloride, calcium sulfate, calcium peroxide, *chlorella* extract, and mixed crude drug extracts can be used.

As specific examples of the phytotoxicity reducing component, for example, those selected from benoxacor, furilazole, dichlormid, dicyclonone, DKA-24 (N1,N2-diallyl-N2-dichloroacetylglycinamide), AD-67 (4-dichloroacetyl-1-oxa-4-azaspiro[4.5]decane), PPG-1292 (2,2-dichloro-N-(1,3-dioxan-2-ylmethyl)-N-(2-propenyl)acetamide), R-29148 (3-dichloroacetyl-2,2,5-trimethyl-1,3-oxazolidine), cloquintcet-mexyl, 1,8-Naphthalic Anhydride, mefenpyr-diethyl, mefenpyr, mefenpyr-ethyl, fenchlorazole-ethyl (fenchlorazole 0 ethyl), MG-191 (2-dichloromethyl-2-methyl-1,3-dioxane), cyometrinil, flurazole, fluxofenim, isoxadifen, isoxadifen-ethyl, MCPA, daimuron, 2,4-D, MON4660 (code No.), oxabetrinil, cyprosulfamide, and TI-35 (code No.) can be used.

Incidentally, in the present invention, for example, in the case of using an oxide or hydroxide of copper, such as copper oxide, cupric hydroxide, etc., these components act as fungicidal components. Namely, in the case where the chemical substance which is used in combination with the microbial pesticide has a fungicidal action, an insecticidal action, an acaricidal action, a nematocidal action, a herbicidal action, a plant growth regulating action, or the like, the at least one member selected from a metal oxide, a metal hydroxide, a metal oxide silicic acid salt, and a metal hydroxide silicic acid salt also acts as a pesticidally active ingredient.

In the microbial pesticidal composition according to the present invention, which comprises a blend of viable spores of *Bacillus subtilis* or *Bacillus amyloliquefaciens* and at least one member selected from a metal oxide, a metal hydroxide, a metal oxide silicic acid salt, and a metal hydroxide silicic acid salt, adjuvant such as a surfactant etc. can be added according to a usual production method of a microbial formulation, as the need arises. Specific examples of the formulation include formulations such as a granule, a dust, a wettable powder, a wettable granule, etc.

Examples of the carrier which is preferable include solid carriers such as talc, bentonite, clay, calcium carbonate, sepiolite, kaolin, diatomaceous earth, white carbon, vermiculite, calcium hydroxide, siliceous sand, ammonium sulfate, urea, pumice, etc.

Examples of the surfactant include nonionic surfactants such as polyethylene glycol higher fatty acid esters, polyoxyethylene alkyl ethers, polyoxyethylene alkyl aryl ethers, polyoxyethylene allyl phenyl ether, sorbitan monoalkylates, etc.; anionic surfactants such as alkyl aryl sulfonic acid salts, dialkyl sulfonic acid salts, lignin sulfonic acid salts, naphthalene sulfonic acid salts and condensates thereof, alkyl sulfuric acid ester salts, alkyl phosphoric acid ester salts, alkyl aryl sulfuric acid ester salts, dialkyl sulfosuccinate salts, alkyl aryl phosphoric acid ester salts, polyoxyethylene alkyl ether sulfuric acid ester salts, polyoxyethylene alkyl aryl ether sulfuric acid ester salts, polyoxyethylene allyl phenyl ether phosphoric acid salts, polycarboxylic acid type polymer active agents, etc.; and furthermore, silicone-based, fluorine-based, and soap surfactants; and the like. Of these surfactants, anionic surfactants are suitably used. In particular, lignin sulfonic acid salts, alkyl allyl sulfonic acid salts, naphthalene sulfonic acid salts, and dialkyl sulfosuccinate-based surfactants are more suitably used.

In the case where a surfactant is blended in the microbial pesticidal composition according to the present invention, the surfactant can be blended in the entirety of the microbial pesticidal composition. However, in the case where the microbial pesticidal composition according to the present invention is a composition in which a micro granule or granule containing viable spores of *Bacillus subtilis* or *Bacillus amyloliquefaciens* is used as an inner core, and the surface of the inner core is covered by at least one member selected from a metal oxide, a metal hydroxide, a metal oxide silicic acid salt, and a metal hydroxide silicic acid salt, the surfactant can be blended only in the inner core; and in addition, the surface of the inner core can be covered (blended only in the cover) by the surfactant together with the at least one member selected from a metal oxide, a metal hydroxide, a metal oxide silicic acid salt, and a metal hydroxide silicic acid salt. The surfactant is blended in the inner core, and the surface of the inner core can be further covered by the surfactant together with the at least one member selected from a metal oxide, a metal hydroxide, a metal oxide silicic acid salt, and a metal hydroxide silicic acid salt.

Examples of other adjuvant include carboxymethyl cellulose, polyethylene glycol, propylene glycol, gum arabic, xanthan gum, and the like; skim milk as a protective agent; a pH buffering agent; and the like.

In the thus obtained microbial pesticidal composition according to the present invention, a water content in the total mass of the composition is preferably less than 2.5% by mass, and more preferably less than 1.5% by mass. In consequence, in the microbial pesticidal composition according to the present invention, the production under low-humidity conditions is advantageous. A water activity (Aw) of the microbial pesticidal composition according to the present invention is preferably less than 0.75, and more preferably less than 0.5. The water activity can be easily determined by measuring an equilibrium relative humidity within an airtight container in which a composition sample is contained hermetically, and it is calculated from the equilibrium relative humidity according to the following equation.

Water activity$(Aw)$=(Equilibrium relative humidity)/100

EXAMPLES

The present invention is specifically described with reference to the following Examples, but it should not be construed that the present invention is limited to these Examples. In the following description, the term "part" is a part by weight.

Production Example 1

Production of Wet Cells

A *Bacillus* sp. D747 strain (FERM BP-8234) which was isolated from the air in Shizuoka-ken, Japan was cultured on a plate medium; an isolated colony was inoculated in a flask and subjected to shaking culture on 20 mL of a bouillon medium (meat extract: 1%, peptone: 1%, sodium chloride: 0.5%) at 27° C. and 120 rpm for one day; thereafter, thus obtained culture liquid was inoculated on 20 L of a medium (comprising) 1% of glucose, 2% of a soluble starch, 0.5% of peptone, 1% of dry yeast, 1% of defatted soybean, 0.2% of $KH_2PO_4$, 0.2% of sodium chloride, and 0.3% of calcium carbonate and having a pH of 6.0 and subjected to shaking culture at 27° C. and 120 rpm for days; thereafter, the strains were collected by centrifugation (10,000×g for 15 minutes) and suspended in sterilized water; and were washed to remove the medium ingredients. This operation was performed twice to obtain wet cells (a sporal fraction) having a wet weight of about 1 kg. This sporal fraction is a fraction containing 50% by weight of spores of *Bacillus* sp. D747 in terms of a dry weight.

Production Example 2

Production of Dry Spores 1 kg of the sporal fraction of *Bacillus* sp. D747 obtained in the foregoing Production Example 1 was suspended in 5 L of distilled water; and thereafter, a diluted solution of the sporal fraction was sprayed while fluidizing 4.5 kg of a powder obtained by pulverizing and mixing 1 part of an alkyl aryl sulfonic acid salt, 10 parts of a lignin sulfonic acid salt, 65 parts of ammonium sulfate, and 15 parts of calcium carbonate by warm air at 60° C. in a fluidized bed pulverizer to achieve fluidized bed granulation, thereby obtaining about 5 kg of a dust-granule mixture of dry spores. Such dry spores contain $1 \times 10^{11}$ cfu/g or more of spores of *Bacillus* sp. D747, and a portion having a desired particle size is separated by means of sieving and then used for each experiment.

Next, representative formulation examples of the microbial pesticidal composition according to the present invention are enumerated, and constitutions, production methods, and the like of formulations are specifically described.

Formulation Example 1

40% of a dust-granule mixture (mean particle diameter: 400 μm) obtained by sieving the dry spores of the *Bacillus* sp. D747 strain obtained in Production Example 2 was mixed with a premix (volume median diameter: 12.7 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 26% of diatomaceous earth, 10% of aluminosilicate (Synthetic Zeolite A-3; a product of Tosoh Corporation, volume median diameter: 16.5 μm), and 1% of clay, to form a wettable powder. The surface of the dust-granular mixture was in a state of being covered by the premix.

Formulation Example 2

40% of a dust-granule mixture (mean particle diameter: 600 μm) obtained by sieving the dry spores of the *Bacillus* sp.

D747 strain obtained in Production Example 2 was mixed with a premix (volume median diameter: 14.8 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 26% of ammonium sulfate, 5% of active alumina (Active Alumina V-R-3; a product of Union Showa K.K., volume median diameter: 12.7 μm), and 6% of clay, to form a wettable powder. The surface of the dust-granule mixture was in a state of being covered by the premix.

Formulation Example 3

90% of a powder portion (mean particle diameter: 100 μm) obtained by sieving the dry spores of the *Bacillus* sp. D747 strain obtained in Production Example 2 was mixed with 10% of active alumina (Active Alumina V-R-3; volume median diameter: 12.7 μm) to form a wettable powder.

Formulation Example 4

90% of a powder portion (mean particle diameter: 100 μm) obtained by sieving the dry spores of the *Bacillus* sp. D747 strain obtained in Production Example 2 was mixed with 10% of magnesium oxide (volume median diameter: 20.1 vim) to form a wettable powder.

Formulation Example 5

90% of a dust-granule mixture (mean particle diameter: 600 μm) obtained by sieving the dry spores of the *Bacillus* sp. D747 strain obtained in Production Example 2 was mixed with 10% of magnesium oxide (volume median diameter: 20.1 μm) to form a wettable powder. The surface of the dust-granule mixture was in a state of being covered by magnesium oxide.

Formulation Example 6

40% of a dust-granule mixture (mean particle diameter: 600 μm) obtained by sieving the dry spores of the *Bacillus* sp. D747 strain obtained in Production Example 2 was mixed with a premix (volume median diameter: 13.9 μm) obtained by uniformly mixing and pulverizing 20% of polyoxin as a bactericidal component, 2% of an alkyl aryl sulfonic acid salt, 5% of magnesium oxide (volume median diameter: 20.1 μm), and 33% of ammonium sulfate, to form a wettable powder. The surface of the dust-granule mixture was in a state of being covered by the premix.

Formulation Example 7

35% of a dust-granule mixture (mean particle diameter: 600 μm) obtained by sieving the dry spores of the *Bacillus* sp. D747 strain obtained in Production Example 2 was mixed with a premix (volume median diameter:6.5 μm) obtained by uniformly mixing and pulverizing 50% of cupric hydroxide (volume median diameter: 3.6 μm), 1.0% of a naphthalene sulfonic acid formalin condensate sodium salt, 6.5% of sodium lignin sulfonate, and 7.5% of ammonium sulfate, to form a wettable powder. The surface of the dust-granule mixture was in a state of being covered by the premix.

Formulation Example 8

35% of a dust-granule mixture (mean particle diameter: 500 μm) obtained by sieving the dry spores of the *Bacillus* sp. D747 strain obtained in Production Example 2 was mixed with a premix (volume median diameter: 7.6 μm) obtained by uniformly mixing and pulverizing 50% of cupric hydroxide (volume median diameter: 5.6 μm), 1.0% of a sodium dialkyl naphthalene sulfonate, 6.5% of sodium lignin sulfonate, and 7.5% of ammonium sulfate, to form a wettable powder. The surface of the dust-granule mixture was in a state of being covered by the premix.

Formulation Example 9

35% of a dust-granule mixture (mean particle diameter: 600 μm) obtained by sieving the dry spores of the *Bacillus* sp. D747 strain obtained in Production Example 2 was mixed with a premix (volume median diameter: 9.8 μm) obtained by uniformly mixing and pulverizing 10% of magnesium hydroxide (volume median diameter: 5.7 μm), 1.0% of a sodium dialkyl naphthalene sulfonate, 6.5% of sodium lignin sulfonate, 40% of ammonium sulfate, and 7.5% of clay, to form a wettable powder. The surface of the dust-granule mixture was in a state of being covered by the premix.

Formulation Example 10

35% of a powder portion (mean particle diameter: 100 μm) obtained by sieving a dust-granule mixture obtained by sieving the dry spores of the *Bacillus* sp. D747 strain obtained in Production Example 2 was mixed with a premix (volume median diameter:7.6 μm) obtained by uniformly mixing and pulverizing 50% of cupric hydroxide (volume median diameter: 5.6 μm), 1.0% of a sodium dialkyl naphthalene sulfonate, 6.5% of sodium lignin sulfonate, and 7.5% of clay, to form a wettable powder.

Formulation Example 11

35% of a powder portion (mean particle diameter: 125 μm) obtained by sieving the dry spores of the *Bacillus* sp. D747 strain obtained in Production Example 2 was mixed with a premix (volume median diameter: 24.2 μm) obtained by uniformly mixing and pulverizing 10% of magnesium oxide (volume median diameter: 20.1 μm), 1.0% of a sodium dialkyl naphthalene sulfonate, 6.5% of sodium lignin sulfonate, 40.0% of ammonium sulfate, and 7.5% of clay, to form a wettable powder.

Formulation Example 12

40% of a dust-granule mixture (mean particle diameter: 600 μm) obtained by sieving the dry spores of the *Bacillus* sp. D747 strain obtained in Production Example 2 was mixed with a premix (volume median diameter: 12.7 μm) obtained by uniformly mixing and pulverizing 20% of mepanipyrim as a fungicide, 1.5% of a naphthalene sulfonic acid formalin condensate sodium salt, 1.5% of a polyoxyethylene alkyl ether, 26% of diatomaceous earth, 10% of aluminosilicate (Synthetic Zeolite A-3; volume median diameter: 16.5 μm), and 1% of clay, to form a wettable powder. The surface of the dust-granule mixture was in a state of being covered by the premix.

Formulation Example 13

40% of a dust-granule mixture (mean particle diameter: 400 μm) obtained by sieving the dry spores of the *Bacillus* sp. D747 strain obtained in Production Example 2 was mixed with a premix (volume median diameter: 10.0 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 26% of diatomaceous earth, 10% of aluminosilicate (Molecular Sieve 13×; a product of Union Showa K.K., volume median diameter: 8.7 μm), and 1% of clay, to form a wettable powder. The surface of the dust-granule spore liquid was in a state of being covered by the premix.

Formulation Example 14

40% of a dust-granule mixture (mean particle diameter: 600 μm) obtained by sieving the dry spores of the *Bacillus* sp. D747 strain obtained in Production Example 2 was mixed with a premix (volume median diameter: 10.0 μm) obtained by uniformly mixing and pulverizing 20% of polyoxin as a bactericidal component, 2% of an alkyl aryl sulfonic acid salt, 10% of aluminosilicate (Molecular Sieve 4A; a product of Union Showa K.K., volume median diameter: 8.3 μm), and 28% of ammonium sulfate, to form a wettable powder. The surface of the dust-granule mixture was in a state of being covered by the premix.

Formulation Example 15

40% of a dust-granule mixture (mean particle diameter: 600 μm) obtained by sieving the dry spores of the *Bacillus* sp. D747 strain obtained in Production Example 2 was mixed with a premix (volume median diameter: 10.0 μm) obtained by uniformly mixing and pulverizing 20% of polyoxin as a fungicidal component, 2% of an alkyl aryl sulfonic acid salt, 10% of aluminosilicate (Molecular Sieve 13×; volume median diameter: 8.7 μm), and 28% of ammonium sulfate, to form a wettable powder.

Formulation Example 16

40% of a dust-granule mixture (mean particle diameter: 600 μm) obtained by sieving the dry spores of the *Bacillus* sp. D747 strain obtained in Production Example 2 was mixed with a premix (volume median diameter: 10.0 μm) obtained by uniformly mixing and pulverizing 20% of polyoxin as a bactericidal component, 2% of an alkyl aryl sulfonic acid salt, 10% of aluminosilicate (Molecular Sieve 3A; a product of Union Showa K.K., volume median diameter: 13.0 μm), and 28% of ammonium sulfate, to form a wettable powder. The surface of the dust-granule mixture was in a state of being covered by the premix.

Formulation Example 17

40% of a powder portion (mean particle diameter: 125 μm) obtained by sieving the dry spores of the *Bacillus* sp. D747 strain obtained in Production Example 2 was mixed with a premix (volume median diameter: 10.0 μm) obtained by uniformly mixing and pulverizing 20% of polyoxin as a bactericidal component, 2% of an alkyl aryl sulfonic acid salt, 10% of aluminosilicate (Molecular Sieve 3A), and 28% of ammonium sulfate, to form a wettable powder.

Formulation Example 18

40% of a powder portion (mean particle diameter: 125 μm) obtained by sieving a dust-granule mixture of the dry spores of the *Bacillus* sp. D747 strain obtained in Production Example 2 was mixed with a premix (volume median diameter: 12.7 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 10% of aluminosilicate (Synthetic Zeolite A-3), 26% of diatomaceous earth, and 1.0% of clay, to form a wettable powder.

Formulation Example 19

40% of a powder portion (mean particle diameter: 125 μm) obtained by sieving the dry spores of the *Bacillus* sp. D747 strain obtained in Production Example 2 was mixed with a premix (volume median diameter: 10.0 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 10% of aluminosilicate (Molecular Sieve 13×), 26% of diatomaceous earth, and 1.0% of clay, to form a wettable powder.

Formulation Example 20

40% of a powder portion (mean particle diameter: 125 μm) obtained by sieving the dry spores of the *Bacillus* sp. D747 strain obtained in Production Example 2 was mixed with a premix (volume median diameter: 14.0 μm) obtained by uniformly mixing and pulverizing 20% of polyoxin as a bactericidal component, 2% of an alkyl aryl sulfonic acid salt, 5% of active alumina (Active Alumina V-R-3), and 33% of ammonium sulfate, to form a wettable powder.

Formulation Example 21

40% of a dust-granule mixture (mean particle diameter: 400 μm) obtained by sieving the dry spores of the *Bacillus* sp. D747 strain obtained in Production Example 2 was mixed with a premix (volume median diameter: 10.0 μm) obtained by uniformly mixing and pulverizing 20% of polyoxin as a bactericidal component, 2% of an alkyl aryl sulfonic acid salt, 10% of aluminosilicate (Molecular Sieve 13×), and 28% of ammonium sulfate, to form a wettable powder. The surface of the dust-granule mixture was in a state of being covered by the premix.

Formulation Example 22

40% of a powder portion (mean particle diameter: 125 μm) obtained by sieving the dry spores of the *Bacillus* sp. D747 strain obtained in Production Example 2 was mixed with a premix (volume median diameter: 10.0 μm) obtained by uniformly mixing and pulverizing 20% of polyoxin as a bactericidal component, 2% of an alkyl aryl sulfonic acid salt, 10% of aluminosilicate (Molecular Sieve 13×), and 28% of ammonium sulfate, to form a wettable powder.

Formulation Example 23

40% of a powder portion (mean particle diameter: 125 μm) obtained by sieving the dry spores of the *Bacillus* sp. D747 strain obtained in Production Example 2 was mixed with a premix (volume median diameter: 14.8 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 5% of active alumina (Active Alumina V-R-3), 26% of ammonium sulfate, and 6.0% of clay, to form a wettable powder.

Formulation Example 24

40% of a dust-granule mixture (mean particle diameter: 250 μm) obtained by sieving the dry spores of the *Bacillus* sp. D747 strain obtained in Production Example 2 was mixed with a premix (volume median diameter: 12.7 μm) obtained by uniformly mixing and pulverizing 20% of polyoxin as a fungicidal component, 2% of an alkyl aryl sulfonic acid salt, 10% of aluminosilicate (Synthetic Zeolite A-3), and 28% of ammonium sulfate, to form a wettable powder. The surface of the dust-granule mixture was in a state of being covered by the premix.

Formulation Example 25

40% of a dust-granule mixture (mean particle diameter: 250 μm) obtained by sieving the dry spores of the *Bacillus* sp. D747 strain obtained in Production Example 2 was mixed with a premix (volume median diameter: 14.8 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 26% of ammonium sulfate, 5% of active alumina (Active Alumina V-R-3), and 6% of clay, to form a wettable powder. The surface of the dust-granule mixture was in a state of being covered by the premix.

Formulation Example 26

35% of a dust-granule mixture (mean particle diameter: 250 μm) obtained by sieving the dry spores of the *Bacillus* sp. D747 strain obtained in Production Example 2 was mixed with a premix (volume median diameter: 7.6 μm) obtained by uniformly mixing and pulverizing 50% of cupric hydroxide (volume median diameter: 5.6 μm), 1.0% of a sodium dialkyl naphthalene sulfonate, 6.5% of sodium lignin sulfonate, and 7.5% of ammonium sulfate, to form a wettable powder. The surface of the dust-granule mixture was in a state of being covered by the premix.

Formulation Example 27

35% of a dust-granule mixture (mean particle diameter: 400 μm) obtained by sieving the dry spores of the *Bacillus* sp. D747 strain obtained in Production Example 2 was mixed with a premix (volume median diameter: 7.6 μm) obtained by uniformly mixing and pulverizing 50% of cupric hydroxide (volume median diameter: 5.6 μm), 1.0% of a sodium dialkyl naphthalene sulfonate, 6.5% of sodium lignin sulfonate, and 7.5% of ammonium sulfate, to form a wettable powder. The surface of the dust-granule mixture was in a state of being covered by the premix.

Formulation Example 28

40% of a dust-granule mixture (mean particle diameter: 250 μm) obtained by sieving the dry spores of the *Bacillus* sp. D747 strain obtained in Production Example 2 was mixed with a premix (volume median diameter: 12.7 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 26% of ammonium sulfate, 10% of aluminosilicate (Synthetic Zeolite A-3), and 1% of clay, to form a wettable powder. The surface of the dust-granule mixture was in a state of being covered by the premix.

Formulation Example 29

40% of a dust-granule mixture (mean particle diameter: 400 μm) obtained by sieving the dry spores of the *Bacillus* sp. D747 strain obtained in Production Example 2 was mixed with a premix (volume median diameter: 14.8 μm) obtained by uniformly mixing and pulverizing 20% of mepanipyrim as a fungicidal component, 1.5% of a naphthalene sulfonic acid formalin condensate sodium salt, 1.5% of a polyoxyethylene alkyl ether, 26% of ammonium sulfate, 5% of active alumina (Active Alumina V-R-3), and 6% of clay, to form a wettable powder. The surface of the dust-granule mixture was in a state of being covered by the premix.

Formulation Example 30

40% of a dust-granule mixture (mean particle diameter: 400 μm) obtained by sieving the dry spores of the *Bacillus* sp. D747 strain obtained in Production Example 2 was mixed with a premix (volume median diameter: 10.0 μm) obtained by uniformly mixing and pulverizing 20% of polyoxin as a bactericidal component, 2% of an alkyl aryl sulfonic acid salt, 10% of aluminosilicate (Molecular Sieve 3A), and 28% of ammonium sulfate, to form a wettable powder. The surface of the dust-granule mixture was in a state of being covered by the premix.

Formulation Example 31

35% of a powder portion (mean particle diameter: 100 μm) obtained by sieving the dry spores of the *Bacillus* sp. D747 strain obtained in Production Example 2 was mixed with a premix (volume median diameter: 7.6 μm) obtained by uniformly mixing and pulverizing 50% of cupric hydroxide (volume median diameter: 5.6 μm), 1.0% of a sodium dialkyl naphthalene sulfonate, 6.5% of sodium lignin sulfonate, and 7.5% of ammonium sulfate, to form a wettable powder.

Comparative Formulation Example 1

40% of a dust-granule mixture (mean particle diameter: 600 μm) obtained by sieving the dry spores of the *Bacillus* sp. D747 strain obtained in Production Example 2 was mixed with a premix (volume median diameter: 13.7 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 36% of diatomaceous earth, and 1% of clay, to form a wettable powder. The surface of the dust-granule spore liquid (in Japanese, funryutai gahoeki) was in a state of being covered by the premix.

Comparative Formulation Example 2

40% of a powder mixture (mean particle diameter: 100 μm) obtained by sieving the dry spores of the *Bacillus* sp. D747 strain obtained in Production Example 2 was mixed with a premix (volume median diameter: 16.0 μm) obtained by uniformly mixing and pulverizing 20% of mepanipyrim as a bactericidal component, 1.5% of a naphthalene sulfonic acid formalin condensate sodium salt, 1.5% of a polyoxyethylene alkyl ether, 36% of ammonium sulfate, and 1% of clay, to form a wettable powder.

Comparative Formulation Example 3

A dust-granule mixture (mean particle diameter: 600 μm) obtained by sieving the dry spores of the *Bacillus* sp. D747 strain obtained in Production Example 2 was used as a wettable powder as it was.

Comparative Formulation Example 4

A dust-granule mixture (mean particle diameter: 400 μm) obtained by sieving the dry spores of the *Bacillus* sp. D747 strain obtained in Production Example 2 was used as a wettable powder as it was.

Comparative Formulation Example 5

A powder mixture (mean particle diameter: 100 μm) obtained by sieving the dry spores of the *Bacillus* sp. D747 strain obtained in Production Example 2 was used as a wettable powder as it was.

Comparative Formulation Example 6

40% of a dust-granule mixture (mean particle diameter: 600 μm) obtained by sieving the dry spores of the *Bacillus* sp. D747 strain obtained in Production Example 2 was mixed with a premix (volume median diameter: 11.9 μm) obtained by uniformly mixing and pulverizing 20% of polyoxin as a bactericidal component, 2% of an alkyl aryl sulfonic acid salt, and 38% of diatomaceous earth, to form a wettable powder. The surface of the dust-granule mixture was in a state of being covered by the premix.

Comparative Formulation Example 7

40% of a powder mixture (mean particle diameter: 100 μm) obtained by sieving the dry spores of the *Bacillus* sp. D747 strain obtained in Production Example 2 was mixed with a premix (volume median diameter: 13.8 μm) obtained by uniformly mixing and pulverizing 20% of polyoxin as a bactericidal component, 2% of an alkyl aryl sulfonic acid salt, and 38% of ammonium sulfate, to form a wettable powder.

Test Example 1

The water content of each of the samples which were made on an experimental basis in the Formulation Examples and Comparative Formulation Examples was measured by the Karl Fischer's method.

Test Example 2

The water activity of each of the samples which were made on an experimental basis in the Formulation Examples and Comparative Formulation Examples was determined by charging 10 g of the sample in a 500-mL airtight container, which was hermetically sealed, and measuring an equilibrium relative humidity within the airtight container at 20° C. The water activity is calculated from the equilibrium relative humidity according to the following equation.

Water activity($Aw$) = (Equilibrium relative humidity)/100

Test Example 3

An airtight package bag containing each of the samples which were made on an experimental basis in the Formulation Examples and Comparative Formulation Examples was allowed to stand at 54° C. for 14 days. In addition, the airtight package bag was allowed to stand in a non-air-conditioned warehouse (room temperature) for 3 years. A rate of decrease of the number of viable cells was calculated from the number of initial viable cells and the number of viable cells after each standing, and the results are shown in Table 1. As for the number of viable cells, the number of viable cells was measured by means of the dilution plate technique with a nutrient agar (broth agar) medium. The medium was cultured at 27° C. for 48 hours to form colonies, and the number of viable cells was presumed from the number of colonies formed. This was designated as a colony-forming unit (cfu) and defined as the number of viable cells per gram of the formulation.

TABLE 1

| | | Water content (%) | Water activity (%) | Rate of decrease of the number of viable cells after standing at 54° C. for 14 days (%) | Rate of decrease of the number of viable cells after standing at room temperature for 3 years (%) |
|---|---|---|---|---|---|
| Formulation Example | 1 | 0.39 | 0.22 | 15 | 24 |
| Formulation Example | 2 | 0.41 | 0.28 | 11 | 17 |
| Formulation Example | 3 | 0.44 | 0.05 | 20 | 31 |
| Formulation Example | 4 | 0.56 | 0.06 | 16 | 28 |
| Formulation Example | 5 | 0.41 | 0.12 | 5 | 9 |
| Formulation Example | 6 | 0.78 | 0.25 | 9 | 22 |
| Formulation Example | 7 | 0.91 | 0.41 | 20 | 9 |
| Formulation Example | 8 | 0.93 | 0.46 | 18 | 7 |
| Formulation Example | 9 | 0.32 | 0.09 | 5 | 15 |
| Formulation Example | 10 | 0.92 | 0.44 | 18 | 36 |
| Formulation Example | 11 | 0.31 | 0.08 | 12 | 22 |
| Formulation Example | 12 | 0.24 | 0.29 | 11 | 19 |
| Formulation Example | 13 | 0.26 | 0.27 | 14 | 23 |
| Formulation Example | 14 | 0.64 | 0.35 | 5 | 12 |
| Formulation Example | 15 | 0.73 | 0.31 | 3 | 17 |
| Formulation Example | 16 | 0.55 | 0.36 | 0 | 9 |
| Formulation Example | 17 | 0.64 | 0.4 | 19 | 43 |
| Formulation Example | 18 | 0.3 | 0.2 | 17 | 42 |
| Formulation Example | 19 | 0.3 | 0.26 | 15 | 39 |
| Formulation Example | 20 | 0.39 | 0.3 | 14 | 39 |
| Formulation Example | 21 | 0.69 | 0.33 | 5 | 25 |
| Formulation Example | 22 | 0.67 | 0.35 | 12 | 40 |
| Formulation Example | 23 | 0.38 | 0.28 | 19 | 39 |
| Formulation Example | 24 | 0.58 | 0.31 | 8 | 36 |
| Formulation Example | 25 | 0.43 | 0.31 | 15 | 33 |
| Formulation Example | 26 | 0.9 | 0.44 | 21 | 10 |
| Formulation Example | 27 | 0.9 | 0.45 | 18 | 7 |
| Formulation Example | 28 | 0.39 | 0.28 | 15 | 35 |
| Formulation Example | 29 | 0.38 | 0.31 | 12 | 19 |
| Formulation Example | 30 | 0.47 | 0.3 | 3 | 11 |
| Formulation Example | 31 | 0.92 | 0.44 | 20 | 34 |
| Comparative Formulation Example | 1 | 1.63 | 0.79 | 96 | 90 |
| Comparative Formulation Example | 2 | 1.69 | 0.88 | 98 | 90 |
| Comparative Formulation Example | 3 | 1.78 | 0.76 | 37 | 43 |
| Comparative Formulation Example | 4 | 1.68 | 0.76 | 40 | 47 |
| Comparative Formulation Example | 5 | 1.61 | 0.81 | 46 | 54 |
| Comparative Formulation Example | 6 | 1.74 | 1.14 | 65 | 76 |
| Comparative Formulation Example | 7 | 1.82 | 1.27 | 73 | 93 |

As is clear from the comparison between the present invention (Formulation Examples) and the comparative example in the above-described tests, in the case of a combined use with at least one member selected from a metal oxide, a metal hydroxide, a metal oxide silicic acid salt, and a metal hydroxide silicic acid salt, the microbial pesticidal composition according to the present invention exhibits excellent preservability without significantly influencing the viability rate.

The present invention is summarized as follows.

That is, an object of the present invention is to provide a microbial pesticidal composition containing viable spores of a bacterium belonging to the genus *Bacillus* and a chemical pesticide, in which the spores can be preserved stably in a living state for a long period of time, and a method for preserving the spores stably in a living state for a long period of time.

Then, by blending viable spores of *Bacillus subtilis* and/or *Bacillus amyloliquefaciens* and at least one member selected from a metal oxide, a metal hydroxide, a metal oxide silicic acid salt, and a metal hydroxide silicic acid salt, a solid microbial pesticidal composition in which the spores are preserved stably for a long period of time is provided.

The invention claimed is:

1. A microbial pesticidal composition, comprising
   an inner core, which is in the form of a micro granule or granule comprising viable spores of *Bacillus subtilis*, *Bacillus amyloliquefaciens*, or both; and
   a surface of the inner core covered by at least one metal-containing compound selected from the group consisting of a metal oxide, a metal hydroxide, a metal oxide silicic acid salt, and a metal hydroxide silicic acid salt, wherein the metal is copper, and
   wherein the microbial pesticidal composition has a water activity at 20° C. of less than 0.5.

2. The microbial pesticidal composition according to claim 1, wherein:
   the inner core is in the form of a micro granule having a mean particle diameter of from 0.05 to 5 mm; and
   a volume median diameter of the at least one metal-containing compound is from 0.01 to 250 μm.

3. The microbial pesticidal composition according to claim 2, wherein a ratio of the mean particle diameter to the volume median diameter ((mean particle diameter of the micro granule)/(volume median diameter of the metal oxide or metal hydroxide)) is from 5 to 750.

4. The microbial pesticidal composition according to claim 1, further comprising a surfactant.

5. The microbial pesticidal composition according to claim 4, wherein the surfactant is blended in the inner core, and the surface of the inner core is also covered by the surfactant together with the at least one metal-containing compound.

6. The microbial pesticidal composition according to claim 4, wherein the surfactant is blended only in the inner core.

7. The microbial pesticidal composition according to claim 4, wherein the surfactant is covered on only the surface of the inner core together with the at least one metal-containing compound.

8. The microbial pesticidal composition according to claim 4, wherein the surfactant is an anionic surfactant.

9. The microbial pesticidal composition according to claim 8, wherein the surfactant is at least one selected from the group consisting of a lignin sulfonic acid salt, an alkylbenzene sulfonic acid salt, a naphthalene sulfonic acid salt, and a dialkyl sulfosuccinate salt.

10. The microbial pesticidal composition according to claim 1, comprising copper hydroxide.

* * * * *